United States Patent [19]

Mustakallio et al.

[11] Patent Number: 4,699,929

[45] Date of Patent: Oct. 13, 1987

[54] PHARMACEUTICAL COMPOSITIONS FOR THE TREATMENT OF SKIN

[75] Inventors: Kimmo K. Mustakallio, Helsinki; Gunnar A. Sothmann, Kirkkonummi; Hanna-Maija Heikinheimo, Espoo, all of Finland

[73] Assignee: Orion-yhtyma Oÿ, Espoo, Finland

[21] Appl. No.: 912,671

[22] PCT Filed: Jul. 8, 1982

[86] PCT No.: PCT/FI82/00026

§ 371 Date: Mar. 8, 1983

§ 102(e) Date: Mar. 8, 1983

[87] PCT Pub. No.: WO83/00084

PCT Pub. Date: Jan. 20, 1983

Related U.S. Application Data

[63] Continuation of Ser. No. 768,172, Aug. 22, 1985, abandoned, which is a continuation of Ser. No. 478,529, Mar. 8, 1983, abandoned.

[30] Foreign Application Priority Data

Jul. 10, 1981 [FI] Finland ................................. 812177

[51] Int. Cl.[4] .................. A61K 31/12; A61K 31/505; A61K 31/35; A61K 31/20

[52] U.S. Cl. ..................................... 514/680; 514/274; 514/454; 514/560; 514/732; 514/789; 424/DIG. 5

[58] Field of Search .................. 514/680; 424/DIG. 5

[56] References Cited

U.S. PATENT DOCUMENTS 3,957,969 5/1976 Fujiyama et al. ............ 424/DIG. 5
4,327,114 4/1982 Brickl et al. ......................... 514/680

FOREIGN PATENT DOCUMENTS 3002089 7/1981 Fed. Rep. of Germany ...... 514/680

Primary Examiner—Jerome D. Goldberg
Assistant Examiner—John M. Kilcoyne
Attorney, Agent, or Firm—Burgess, Ryan & Wayne

[57] ABSTRACT

Pharmaceutical compositions for the treatment of skin have been prepared in a carrier which contains 40 to 60% of liquid paraffin, 40 to 60% of solid paraffin, and 0.5 to 5% of microcrystalline wax. The new carrier is especially suitable for readily oxidizable drugs such as dithranol and its derivatives. From the compositions of the invention it is possible to prepare sufficiently thin and hard, yet non-brittle sticks by means of which the drug can be applied at precisely the desired point of the skin.

13 Claims, No Drawings

PHARMACEUTICAL COMPOSITIONS FOR THE TREATMENT OF SKIN

This is a continuation of application Ser. No. 768,172, filed on Aug. 22, 1985 and now abandoned, which is a continuation of application Ser. No. 478,529, filed Mar. 8, 1983, also now abandoned.

The present invention is concerned with new paraffin-based pharmaceutical compositions to be applied to the skin. The invention is particularly concerned with compositions containing readily oxidizable drugs such as dithranol and its derivatives.

One of the drawbacks of the ointment bases used in the treatment of skin diseases is a tendency to spread from the affected skin to the surrounding healthy skin and to clothes. This is particularly detrimental when poorly penetrating ointments are used which contain vaseline, paraffin oil, and soft waxes and which mainly affect the horny layer and the epidermis. It is almost impossible to direct such ointments to the affected skin areas only, and dosage is difficult and extremely variable. This causes problems, especially if the ointment includes agents which irritate the skin or which colour the skin and clothes. One substance that affects the colours healthy skin is dithranol, or anthranil, still the most commonly used pharmaceutical for the topical treatment of psoriasis.

P. G. Unna was the first scientist to develop ointment sticks containing dermatological agents in an attempt to reduce the above drawbacks /Monatschefte fur Praktische Dermatologi 1886:5 157–167/. According to Unna, dry, localised, spot-like skin diseases, such as psoriasis, dry eczemas, and spotty fungal skin diseases are best suited for treatment with ointment sticks. He suggests that the consistency of the ointment stick be sufficiently soft so that little force is needed to apply a stripe of ointment to the skin but, on the other hand, sufficiently hard so that the stick is not deformed when used or when exposed to high temperatures. According to him, these requirements, though dependent on the pharmaceutical used, could be satisfied by mixtures of olive oil and wax. Unna used colophonium as a hardening agent in addition to wax. Unna used yellow beeswax (cera flava). Of the ointment stick formulae suggested by Unna, almost all of which had stick bases of similar compositions, the following two deserve mention: "Stilus acid. salicyl. unguens 10%" (Acid. salicyl. praec. 10.0, Colophoni 5.0, Cerae flavae 45.0, Ol. oliv. prov. 40.0) and "Stilus Chrysarobini unguens 30%" (Chrysarobini 30.0, Colophoni 5.0, Cerae flavae 35.0, Ol. oliv. prov. 30.0).

Unna also developed a paraffin ointment stick (Paraffini solid. 50.0, Paraffini liquid. 50.0), but, owing to the softness of the stick he did not mix any pharmaceutical into the stick, but used the stick for oiling dry, horny skin in the way a lip pomada is used.

Since Unna's pioneering work, there have been very few papers on ointment sticks in the treatment of skin diseases.

In 1941, F. Dietel mentioned the chrysarobin ointment stick for the treatment of psoriasis /Deutsche medizinische Wochenschrift 1941:9 237–9/. The composition of the stick was: Chrysarobin 30.0, Cerae flav. 20.0, Adipis lanae 50.0.

In 1962 and 1966, there were two papers in which a close relative of chrysarobin, cignolin (or dithranol) was used in ointment sticks/Weber, G., Medizinische Welt 1962:35 1839–40 and Schafé, M. K., Zeitschrift fur Hautund Geschlechtskrankheiten 1966 XL 347–51/. In both papers, the same commercial preparation "Psoriacid" was used. The exact composition of the ointment base was not given, but it included Vaselinium album, Adeps lanae, Paraff. solidum suffanita and Cera alba.

In 1970, F. Novotný used the following ointment stick base in his study: Oleum ricini 1.0, Paraffinum liquidum 4.0, Cera flava 43.0, Oleum cacao 52.0, /Cs. Derm. 45 (1970):1 20–22/.

At present, only one ointment stick is available as a commercial preparation in the Nordic countries. This is an "Anthraderm" stick containing 0.5, 1.0 or 2.0% dithranol (Pharma-medica). The composition of the ointment base has not been given as a percentage, but the base contains wool alcohols, cocoa oil, white beeswax, whale wax (cetaceum), and peanut oil (oleum arachidis) as well as 0.5% salicylic acid and 0.02% butylated hydroxytoluene as stabilizers.

Even though stick-shaped preparations would be a good dosage form for several dermatological medicines in view of the treatment, they have not obtained a position of major importance in practice. This is because the ointment stick bases so far developed have been too soft and have contained oxidizable vegetable oils and animal fats. Rancid, peroxidating oils and fats, in turn, oxidize many pharmaceutical substances such as dithranol and chrysarobin resulting in ineffective compounds. Unna stated in his monography discussing dithranol that, in the presence of oxygen, the most important fatty acid in olive oil—oleic acid—converts both chrysarobin and dithranol into dark, coloured compounds. It has also been noticed that the oxidation of dithranol is faster, the more double bonds the fatty acid molecule contains.

Some sticks also have the drawback that they contain wool grease, which can cause contact allergy.

These problems are associated with the "Anthraderm" stick. The unsaturated fatty acids included in peanut oil and cocoa oil oxidize after the opening of the package and oxidize the dithranol into a dark, ineffective dimer. In spite of the antioxidants in the stick it must be stored in a cool place and used within 6 months of opening.

It has now been discovered that a paraffin ointment base which contains about 40 to 60% of liquid paraffin (white vaseline), about 40 to 60% of solid paraffin, and about 0.5 to 5% of microcrystalline paraffin wax is a very good vehicle for stick-shaped dermatological preparations. The essential aspect of the invention is the use of microwax as a hardening agent. The stick cannot be hardened by increasing the proportion of solid paraffin, because the stick then tends to be brittle.

It has also been noticed that the carrier agent is particularly suitable for readily oxidizable pharmaceuticals such as dithranol. In paraffin ointments the storage stability of such agents is better than in ointments containing unsaturated fats, because oxidation via peroxidation is excluded. However, it is surprising that, when microwax is added to a mixture of liquid and hard paraffin, ointment bases are obtained that given even better protection against oxidation.

The liquid paraffin used in pharmacy (Paraffinum subliquidum) is a mixture of liquid hydrocarbons with a high boiling point (above 300°). It is commonly used for various ointments.

The solid paraffin (Paraffinum solidum) is a mixture of solid hydrocarbons mainly containing straight-chain alkales; the melting point of the mixture is from 50° to 57°. It is used in various ointments as a hardening agent.

Microcrystalline waxes are mixtures of hydrocarbons whose melting point is from 60° to 90° and which mainly contain cyclic hydrocarbons, some branched acyclic alkanes, but very few n-alkanes. Their crystal structure is considerably more delicate than that of paraffin waxes. They have been used as a coating agent for papers, textiles, metals and plastics. Microwaxes have also been used in wax coatings of cheese, in chewing gums and sweets, in cosmetic products such as lipsticks, skin ointments and hair sprays, rubber glues, car, floor polishes, in crayons, and in candles.

In the ointment base presented here, microwaxes whose melting points are in the range 75° to 90°, in particular about 85° to 88°, will be used.

The composition of the ointment base varies depending on the materials used, the desired hardness and toughness, and on the pharmaceutical to be used and its concentration. A composition is recommended that contains about 45 to 55%, in particular about 48 to 51%, liquid paraffin, about 45 to 55%, in particular about 47 to 50%, solid paraffin, and about 1 to 3%, in particular about 1.5 to 2.5%, microwax.

If desired, stabilizers and other additives may be added.

From the mixture presented here, it is possible to prepare sufficiently thin and hard, yet non-brittle sticks which adhere well to the skin and by means of which the preparation can be applied at precisely the desired point. The preparation is better than conventional ointment bases, because the stick does not feel greasy. Moreover, the pharmaceutical remains on the desired area on the skin and does not spread to the healthy skin or adhere to clothes to the same extent as from conventional ointment bases. So far, dithranol has mainly been used in hospital treatment. The sticks presented here also permit treatment at home.

Readily oxidizable pharmaceuticals such as dithranol and chrysarobin keep well in the ointment bases presented here.

Pharmaceuticals that can be used in the ointment bases presented here include dithranol, 10-acyl derivatives of dithranol, chrysarobin, podophyllin, topical cytostats (e.g. 5-fluorouracil), idoxuridine, benzoylperoxine, and tretinoin.

In order to study storage stability, tests were performed on different dithranol preparations. Dithranol is well known for its poor stability. Attempts have been made to stabilize dithranol preparations in various ways, e.g. by adding salicylic acid, but the resulting preparations have not been pleasant to use.

In the stability tests, the stick presented here was compared with two paraffin-based dithranol ointments as well as with the "Anthraderm"-stick.

In Table 1, a dithranol preparation in accordance with the invention is compared with two paraffin-based preparations of the same concentration. The results indicate that in the ointment base presented here stability is better than in ointments containing vaseline or paraffin exclusively.

TABLE 1

Change in dithranol content during storage in an ointment base prepared according to the invention and in two ointment bases (3.0% preparation)

| Storage period (months) | Ointment base as per invention (Ex. 1) | Ointment I (Vas. fl. 99.0%, Par. sol. 1.0%) | Ointment II (Par. sol. 25.8% Par. liq. 74.2%) |
|---|---|---|---|
| 2 | +1.9 | −2.1 | −3.4 |
| 5 | +1.4 | −1.7 | −0.3 |

In Table 2, the new preparation was compared with the commercial "Anthraderm" preparation by determining the concentrations of quinone and dimer formed in the preparations during storage. It can be seen that the storage stability of the preparation presented here is considerably better in spite of the fact that it does not contain any stabilizing agents.

TABLE 2

Quinone and dimer concentrations (%) in dithranol preparation according to the invention and in the commercial "Anthraderm" preparation during storage

| Temperature °C. | Time (months) | Preparation as per the invention | | "Anthraderm" | |
|---|---|---|---|---|---|
| | | Quinone | Dimer | Quinone | Dimer |
| Room temp. | 3 | 2 to 5 | 2 to 5 | ca 10 | 10 to 20 |
| " | 5 | 2 to 5 | 2 to 5 | ca 10 | 10 to 20 |
| 35° | 2 | 2 to 5 | 2 to 5 | | |
| " | 5 | 2 to 5 | 2 to 5 | | |

The following examples will illustrate the invention.

EXAMPLE 1

| Dithranol. | 3.0 |
|---|---|
| Paraffin. liq. | 48.0 |
| Paraffin. solid. | 47.0 |
| Microwax (Acrowax 9240 G) | 2.0 |

The preparation is as follows: The base proper, the paraffins and the microwax, are melted and mixed. The active agent is added to the mixture, and the mixture is cast into appropriate moulds or into packages which also function as casting moulds.

EXAMPLE 2

| Chrysarobin. | 15.0 |
|---|---|
| Paraff. liq. | 42.0 |
| Paraff. sol. | 40.0 |
| "Acrowax 9240 G" | 3.0 |

EXAMPLE 3

| Podofyllin. | 1.0 |
|---|---|
| Paraff. liq. | 49.0 |
| Paraff. sol. | 48.0 |
| "Acrowax 9240 G" | 2.0 |

EXAMPLE 4

| Idoxuridine | 3.0 |
|---|---|
| Paraff. liq. | 48.0 |
| Paraff. sol. | 47.0 |
| "Acrowax 9240 G" | 2.0 |

What is claimed is:

1. A pharmaceutical composition consisting of a therapeutically effective amount of an otherwise readily oxidizable drug for the treatment of skin contained in a carrier, said carrier consisting of about 40 to 60% liquid paraffin, about 40 to 60% solid paraffin, and about 0.5 to 5% microcrystalline wax, said drug being substantially stable against oxidation when contained in said carrier, said readily oxidizable drug being selected from the group consisting of dithranol, 10-acyl dithranol, chrysarobin, podophyllin, 5-fluorouracil, idoxuridine, benzoylperoxine, and tretinoin.

2. A composition according to claim 1 wherein the carrier consists of about 45 to 55% of liquid paraffin, about 45 to 55% of solid paraffin, and about 1 to 3% of microcrystalline wax.

3. A composition according to claim 2 wherein the carrier consists of about 48 to 51% of liquid paraffin, about 47 to 50% of solid paraffin, and about 1.5 to 2.5% of microcrystalline wax.

4. A composition according to claim 1 wherein said composition is in a stick-shaped form.

5. A composition according to claim 1 wherein the melting point of the microcrystalline wax is about 75° to 90° C.

6. A composition according to claim 5 wherein the melting point of the microcrystalline wax is about 85° to 88° C.

7. A composition according to claim 2 wherein the melting point of the microcrystalline wax is about 75° to 90° C.

8. A composition according to claim 3 wherein the melting point of the microcrystalline wax is about 75° to 90° C.

9. A composition according to claim 7 wherein the melting point of the microcrystalline wax is about 85° to 88° C.

10. A composition according to claim 8 wherein the melting point of the microcrystalline wax is about 85° to 88° C.

11. A composition according to claim 2 wherein the drug is dithranol.

12. A composition according to claim 2 wherein the drug is 10-acyl dithranol.

13. A composition according to claim 12 wherein the carrier consists of about 49.5% of liquid paraffin, about 48.5% of solid paraffin, and about 2.0% of microcrystalline wax whose melting point is about 85° to 88° C.

* * * * *